US012090041B2

(12) United States Patent
Dake et al.

(10) Patent No.: US 12,090,041 B2
(45) Date of Patent: Sep. 17, 2024

(54) BRANCHED STENT GRAFT DEVICE AND DEPLOYMENT

(71) Applicant: W. L. Gore & Associates, Inc., Newark, DE (US)

(72) Inventors: Michael D. Dake, Stanford, CA (US); Joshua J. Lovekamp, Phoenix, AZ (US); Michael C. Nilson, Flagstaff, AZ (US); Edward E. Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 18/125,910

(22) Filed: Mar. 24, 2023

(65) Prior Publication Data

US 2024/0099826 A1    Mar. 28, 2024

Related U.S. Application Data

(60) Continuation of application No. 16/774,558, filed on Jan. 28, 2020, now Pat. No. 11,638,639, which is a
(Continued)

(51) Int. Cl.
*A61F 2/07* (2013.01)
*A61F 2/06* (2013.01)
(Continued)

(52) U.S. Cl.
CPC ............... *A61F 2/07* (2013.01); *A61F 2/844* (2013.01); *A61F 2/954* (2013.01);
(Continued)

(58) Field of Classification Search
CPC .... A61F 2/07; A61F 2/844; A61F 2/90; A61F 2/962; A61F 2002/061; A61F 2002/067
See application file for complete search history.

(56) References Cited

U.S. PATENT DOCUMENTS

| 5,476,589 A | 12/1995 | Bacino |
| 5,919,225 A | 7/1999 | Lau et al. |

(Continued)

FOREIGN PATENT DOCUMENTS

| AU | 2010202544 B1 | 8/2010 |
| JP | 2014-526929 A | 10/2014 |

(Continued)

OTHER PUBLICATIONS

International Preliminary Report on Patentability received for PCT Patent Application No. PCT/US2012/050816, mailed on Feb. 27, 2014, 9 pages.

(Continued)

*Primary Examiner* — Sarah W Aleman

(57) ABSTRACT

A device for treating disease along a main vessel and at least one branch vessel extending from the main vessel includes a branch member for deployment in the branch vessel, the branch member having a branch lumen; and a main body for deployment in the main vessel. The main body has a generally tubular wall extending generally longitudinally between opposite first and second ends. The wall has an internal surface defining a main lumen and an opposite outer surface. The wall has a recessed portion that is recessed relative to the outer surface of the wall and positioned between the first and second ends of the main body. The main body has an opening formed in the recessed portion of the wall for receiving the branch member therethrough such that the branch lumen is in fluid communication with the main lumen.

23 Claims, 6 Drawing Sheets

Related U.S. Application Data continuation of application No. 15/072,037, filed on Mar. 16, 2016, now Pat. No. 10,588,735, which is a division of application No. 13/584,650, filed on Aug. 13, 2012, now Pat. No. 9,314,328.

(60) Provisional application No. 61/524,256, filed on Aug. 16, 2011.

(51) Int. Cl.
  *A61F 2/844* (2013.01)
  *A61F 2/954* (2013.01)
  *A61F 2/90* (2013.01)

(52) U.S. Cl.
  CPC ... *A61F 2002/061* (2013.01); *A61F 2002/065* (2013.01); *A61F 2002/067* (2013.01); *A61F 2/90* (2013.01); *F04C 2270/0421* (2013.01)

(56) References Cited

U.S. PATENT DOCUMENTS

| | | | |
|---|---|---|---|
| 5,925,075 | A | 7/1999 | Myers et al. |
| 6,042,605 | A | 3/2000 | Martin et al. |
| 6,551,350 | B1 | 4/2003 | Thornton et al. |
| 6,645,242 | B1 | 11/2003 | Quinn |
| 6,814,752 | B1 | 11/2004 | Chuter |
| 7,189,257 | B2 | 3/2007 | Schmitt et al. |
| 7,691,141 | B2 | 4/2010 | Lewis et al. |
| 8,021,419 | B2 | 9/2011 | Hartley et al. |
| 8,080,051 | B2 | 12/2011 | Lewis et al. |
| 8,221,487 | B2 | 7/2012 | Lewis et al. |
| 8,556,961 | B2 | 10/2013 | Quinn |
| 8,753,386 | B2 | 6/2014 | Shaw |
| 9,005,267 | B2 | 4/2015 | Greenberg et al. |
| 9,314,328 | B2 | 4/2016 | Dake et al. |
| 9,381,078 | B2 | 7/2016 | Greenberg et al. |
| 9,629,738 | B2 | 4/2017 | Kelly |
| 10,588,735 | B2 | 3/2020 | Dake et al. |
| 11,638,639 | B2 | 5/2023 | Dake et al. |
| 2003/0120263 | A1 | 6/2003 | Ouriel et al. |
| 2005/0010277 | A1 | 1/2005 | Chuter |
| 2005/0110277 | A1 | 5/2005 | Adamson et al. |
| 2005/0131517 | A1 | 6/2005 | Hartley et al. |
| 2006/0155359 | A1 | 7/2006 | Watson |
| 2006/0184228 | A1* | 8/2006 | Khoury ............... A61F 2/915 623/1.13 |
| 2006/0229707 | A1 | 10/2006 | Khoury |
| 2007/0219621 | A1 | 9/2007 | Hartley et al. |
| 2007/0233229 | A1 | 10/2007 | Berra et al. |
| 2007/0250152 | A1 | 10/2007 | Xiao et al. |
| 2008/0097578 | A1 | 4/2008 | Erickson et al. |
| 2008/0114444 | A1 | 5/2008 | Yu |
| 2008/0114446 | A1 | 5/2008 | Hartley et al. |
| 2008/0269866 | A1 | 10/2008 | Hamer et al. |
| 2008/0269867 | A1 | 10/2008 | Johnson |
| 2008/0281399 | A1 | 11/2008 | Hartley et al. |
| 2009/0043377 | A1* | 2/2009 | Greenberg ............... A61F 2/07 623/1.35 |
| 2009/0048663 | A1 | 2/2009 | Greenberg |
| 2009/0093873 | A1 | 4/2009 | Navia |
| 2009/0157164 | A1 | 6/2009 | McKinsey et al. |
| 2009/0240316 | A1 | 9/2009 | Bruszewski |
| 2009/0259290 | A1 | 10/2009 | Bruszewski et al. |
| 2009/0319022 | A1 | 12/2009 | Hartley et al. |
| 2010/0042201 | A1 | 2/2010 | Sherif |
| 2010/0161025 | A1 | 6/2010 | Kuppurathanam et al. |
| 2011/0054594 | A1 | 3/2011 | Mayberry et al. |
| 2011/0087318 | A1 | 4/2011 | Daugherty et al. |
| 2011/0257731 | A1* | 10/2011 | Hartley ............... A61F 2/07 623/1.35 |
| 2011/0313512 | A1* | 12/2011 | Hartley ............... A61F 2/07 623/1.35 |
| 2012/0271401 | A1 | 10/2012 | Bruszewski et al. |
| 2013/0184806 | A1 | 7/2013 | Arbefeuille et al. |
| 2013/0211506 | A1 | 8/2013 | Dake et al. |
| 2013/0274850 | A1 | 10/2013 | Kelly |
| 2014/0135905 | A1 | 5/2014 | Hung et al. |
| 2016/0193032 | A1 | 7/2016 | Dake et al. |
| 2019/0380851 | A1 | 12/2019 | Bertini et al. |
| 2020/0163751 | A1 | 5/2020 | Dake et al. |
| 2023/0255743 | A1 | 8/2023 | Birdno et al. |

FOREIGN PATENT DOCUMENTS

| | | |
|---|---|---|
| WO | 2005/034809 A1 | 4/2005 |
| WO | 2008/021557 A1 | 2/2008 |
| WO | 2008/130503 A2 | 10/2008 |
| WO | 2010/024879 A1 | 3/2010 |
| WO | 2013/025727 A1 | 2/2013 |
| WO | 2013/074990 A1 | 5/2013 |
| WO | 2017/205486 A1 | 11/2017 |

OTHER PUBLICATIONS

International Search Report and Written Opinion for PCT/US2012/050816 mailed Nov. 15, 2012, corresponding to U.S. Appl. No. 13/584,650.

Office Action received for European Patent Application No. 12750957.8, mailed on Jul. 27, 2018, 6 pages.

International Preliminary Report on Patentability received for PCT Patent Application No. PCT/US2021/036844, mailed on Dec. 22, 2022, 9 pages.

International Search Report and Written Opinion received for PCT Patent Application No. PCT/US2021/036844, mailed on Sep. 21, 2021, 12 pages.

* cited by examiner

BRANCHED STENT GRAFT DEVICE AND DEPLOYMENT

CROSS REFERENCE RELATED APPLICATIONS

This patent application is a Continuation of U.S. Ser. No. 16/774,558, filed Jan. 28, 2020, which is a Continuation of U.S. patent application Ser. No. 15/072,037, filed Mar. 16, 2016, now U.S. Pat. No. 10,588,735, issued Mar. 17, 2020, which is a Divisional of U.S. patent application Ser. No. 13/584,650, filed Aug. 13, 2012, now U.S. Pat. No. 9,314,328, issued Apr. 19, 2016, which claims priority to and the benefit of U.S. Provisional Patent Application No. 61/524,256 filed on Aug. 16, 2011, all of which are incorporated herein by reference in their entireties for all purposes.

BACKGROUND

Field

The present disclosure relates to stent grafts for treating disease of the vasculature and, more particular, to stent graft devices and methods of deployment of the same for treating disease of branched vasculature.

Discussion of the Related Art

Disease of the vasculature is increasingly common and, because of the tortuous nature and complexity of the vasculature, is difficult for medical practitioners to treat. By way of example, aortic dissections commonly begin at or near the aortic valve root and continue to the ascending aorta and the aortic arch, and may also affect the upper part of the descending aorta. The three branch vessels off the aortic arch, namely, the brachiocephalic (innominate) artery and the left common carotid and left subclavian arteries, are anatomically difficult for medical practitioners to access and ultimately treat effectively.

It remains desirable to provide improved devices, delivery systems and methods for repairing disease along the aorta and branches extending therefrom.

DETAILED DESCRIPTION

The present disclosure provides an improved, less invasive, and simplified device, system and method for treating disease of the vasculature, particularly along a main vessel and related branch vessels.

Throughout this specification and in the claims, it should be readily appreciated that the term "branch vessel" refers to a vessel that branches outwardly from a main vessel. The "branch vessels" extending from the aortic arch, for example, include the brachiocephalic artery, the left common carotid and left subclavian arteries. Other "branch vessels" extending from the aorta include, but are not limited to: the celiac, inferior phrenic, superior mesenteric, lumbar, inferior mesenteric, middle sacral, middle suprarenal, renal, internal spermatic, ovarian (in the female), and innominate. As another example, the hypogastric artery is a branch vessel to the common iliac, which is a main vessel in this context. Thus, it should be seen that "branch vessel" and "main vessel" are relative terms.

When discussing application of the present disclosure to the aorta or other blood vessels, the term "distal" with respect to such devices is intended to refer to a location that is, or a portion of the device that when implanted is, further downstream with respect to blood flow; the term "distally" means in the direction of blood flow or further downstream.

The term "proximal" is intended to refer to a location that is, or a portion of the device that when implanted, is further upstream with respect to blood flow; the term "proximally" means in the direction opposite to the direction of blood flow or further upstream.

Figure 1:
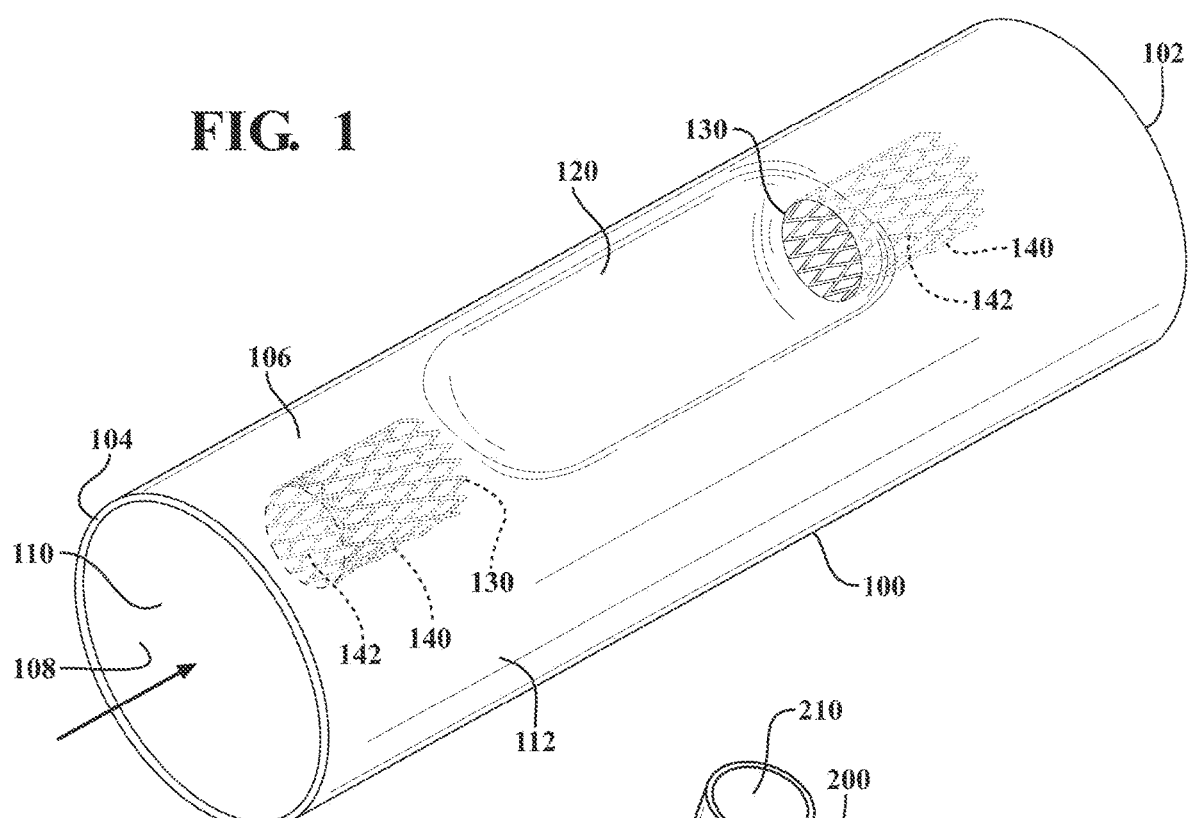
FIG. 1 is a perspective view of a main body of a branched device in accordance with exemplary embodiments for treating a vessel and branch vessels extending outwardly therefrom.
Figure 2:
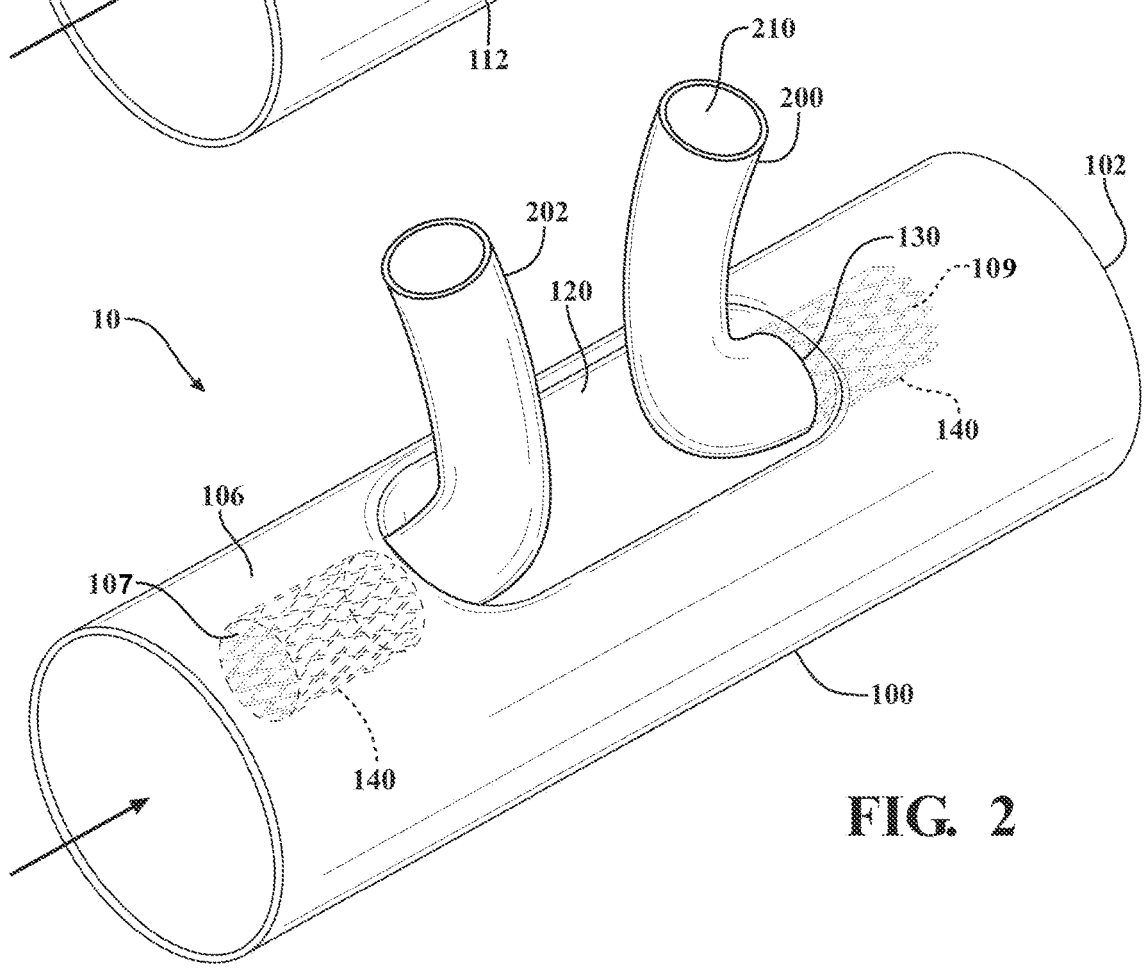
FIG. 2 is a perspective view of the branched device of FIG. 1 showing branch members extending through openings in a recessed portion of the main body

A device in accordance with various embodiments for treating disease along a main vessel and at least one branch vessel extending from the main vessel is shown and generally indicated at 10 in FIGS. 1 and 2. The device 10 includes a main body 100 for deployment in the main vessel and having a main lumen 110. The device 10 also includes at least one branch member 200 for deployment in the at least one branch vessel and having a branch lumen 210.

The main body 100 of the device 10 has opposite first 102 and second 104 ends, and a wall 106 extending generally longitudinally between the first 102 and second 104 ends. The wall 106 has an internal surface 108 that defines the main lumen 110. The wall 106 also has an outer surface 112 opposite the inner surface 108.

The wall 106 includes a recessed portion 120 that is recessed relative to the outer surface 112 of the wall 106 and positioned between the first 102 and second 104 ends of the main body 100. The main body 100 further includes at least one opening 130 formed in the recessed portion 120 of the wall 106 that receives the at least one branch member 200 therethrough such that the branch lumen 210 is in fluid communication with the main lumen 110.

In various embodiments, one or more support walls can be incorporated into the main body, each for supporting a branch member extending through an opening in the recessed portion of the wall. A support wall can have any preferred length, diameter, wall thickness or secondary lumen shape, such as an oval, polygon or "D shape". Support walls can incorporate a support member such as a stent. A support wall can incorporate a support wall to branch member attachment feature such as a hook anchor, flared stent apex, or other securing means commonly known in the art. A secondary lumen can be tapered along its length and can include radiopaque markers. As shown in FIGS. 1 and 2, for example, the main body 100 can include a generally tubular support wall 140 that extends from each opening 130 toward one of the first 102 and second 104 ends of the main body 100 Each support wall 140 forms a secondary lumen 142, which receives one of the at least one branch members 200 therethrough such that the branch lumen 210 is in fluid communication with the main lumen 110.

In various embodiments, for example as illustrated in FIG. 2, multiple support walls 140 and secondary lumens 142, incorporated into a single main body 100, can be oriented in generally opposing directions relative to the support wall longitudinal axis. A first support wall and secondary lumen having a first longitudinal orientation will therefore define a first blood flow direction. A "blood flow direction" is defined as the direction defined by the blood flow as it enters into a secondary lumen open end, as generally indicated at 107, 109 in FIG. 2. A second support wall and secondary lumen having a second longitudinal orientation will therefore define a second blood flow direction. The first and second blood flow directions can, if desired, be oriented 180° from each other as depicted in FIG. 2. Further details on internal support walls for supporting branch members extending through openings in the main body are disclosed in U.S. Pat. No. 6,645,242 to Quinn, the contents of which are hereby incorporated by reference in its entirety.

In other exemplary embodiments, the device may be used for treating disease along an aortic arch and a plurality of branch vessels extending from the aortic arch. In the particular embodiment illustrated in FIGS. 1 and 2, a pair of openings 130 is formed in the recessed portion 120 of the wall 106 and disposed on generally opposite sides of the recessed portion 120 for treating, for example, the aortic arch and the left subclavian and brachiocephalic arteries with the branch members 200, 202. It should be appreciated that the openings may be positioned near or adjacent to each other for treating different combinations of branch arteries, such as the left common carotid and left subclavian arteries.

Figure 3:
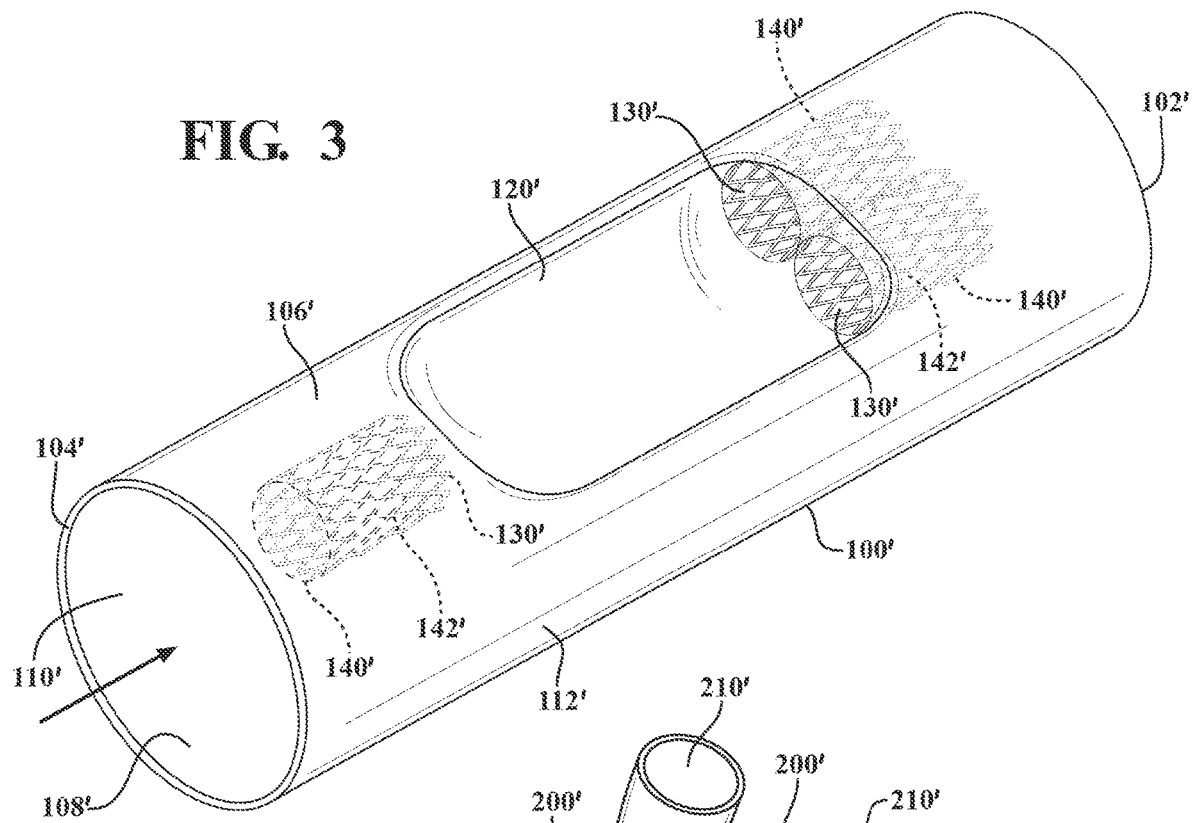
FIG. 3 is a perspective view of a main body of a branched device in accordance with exemplary embodiments for treating a vessel and branch vessels extending outwardly therefrom.
Figure 4:
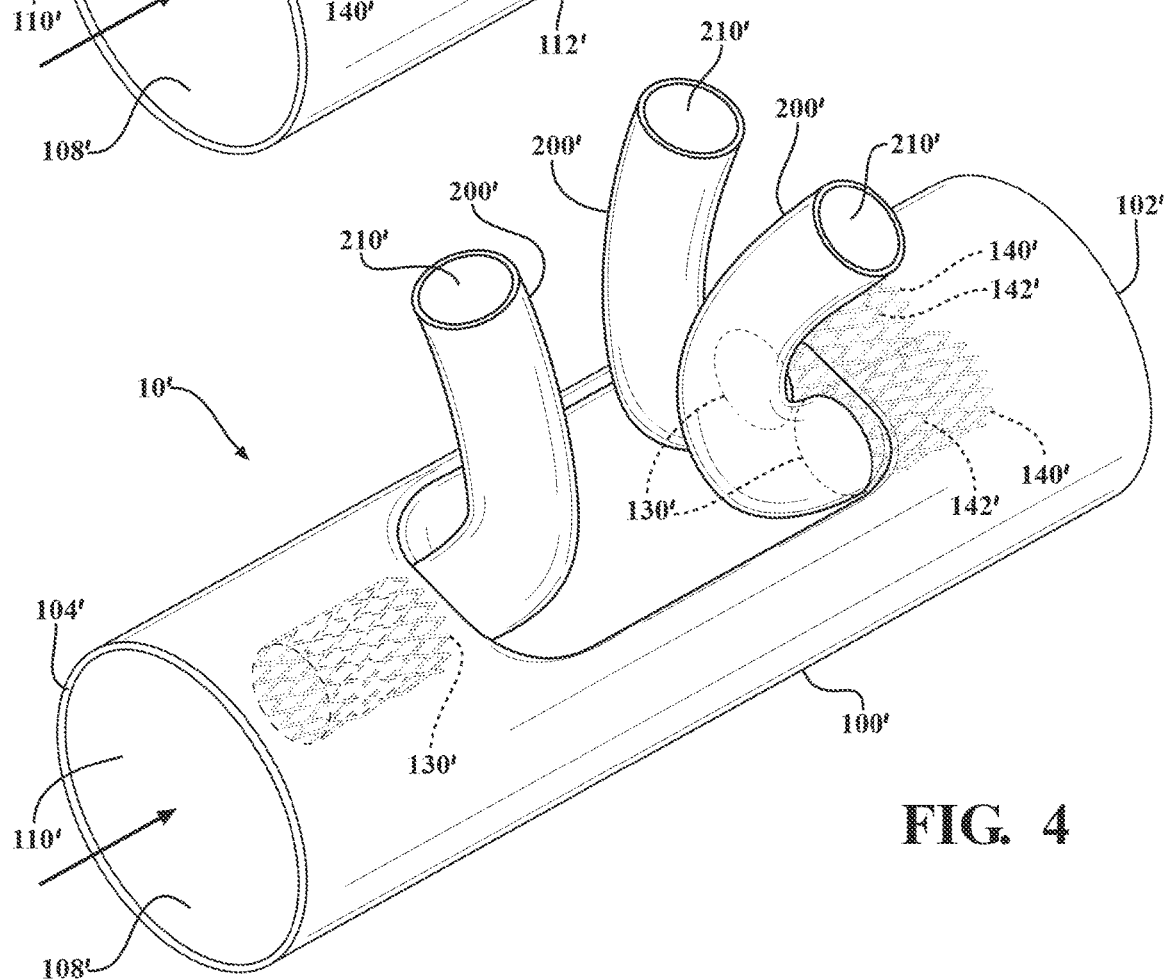
FIG. 4 is a perspective view of the branched device of FIG. 3 showing branch members extending through openings in a recessed portion of the main body.

Referring to FIGS. 3 and 4, wherein like prime numerals indicate like parts from previously described exemplary embodiments, the device 10' may include a main body 100' for deployment in the aortic arch and a plurality of branch members 200' each for deployment in one of the plurality of branch vessels extending from the aortic arch, including the brachiocephalic, the left common carotid and left subclavian arteries. The main body 100' has a plurality of openings 130' formed in the recessed portion 120' of the wall 106'. Each branch member 200' has a branch lumen 210' and extends respectively through one of the plurality of openings 130' such that each branch lumen 210' is in fluid communication with the main lumen 110'.

In accordance with other exemplary embodiments, a method for deploying the device to a treatment site for treating disease along a main vessel and at least one branch vessel extending from the main vessel is described below in connection with FIGS. 5 through 9. The embodiments shown in FIGS. 5-9 and described illustrate deployment of the device along the aortic arch and related branch vessels, though it should be appreciated that use and deployment of the device may be applied to other branched treatment sites along the aortic vasculature.

Figure 5:
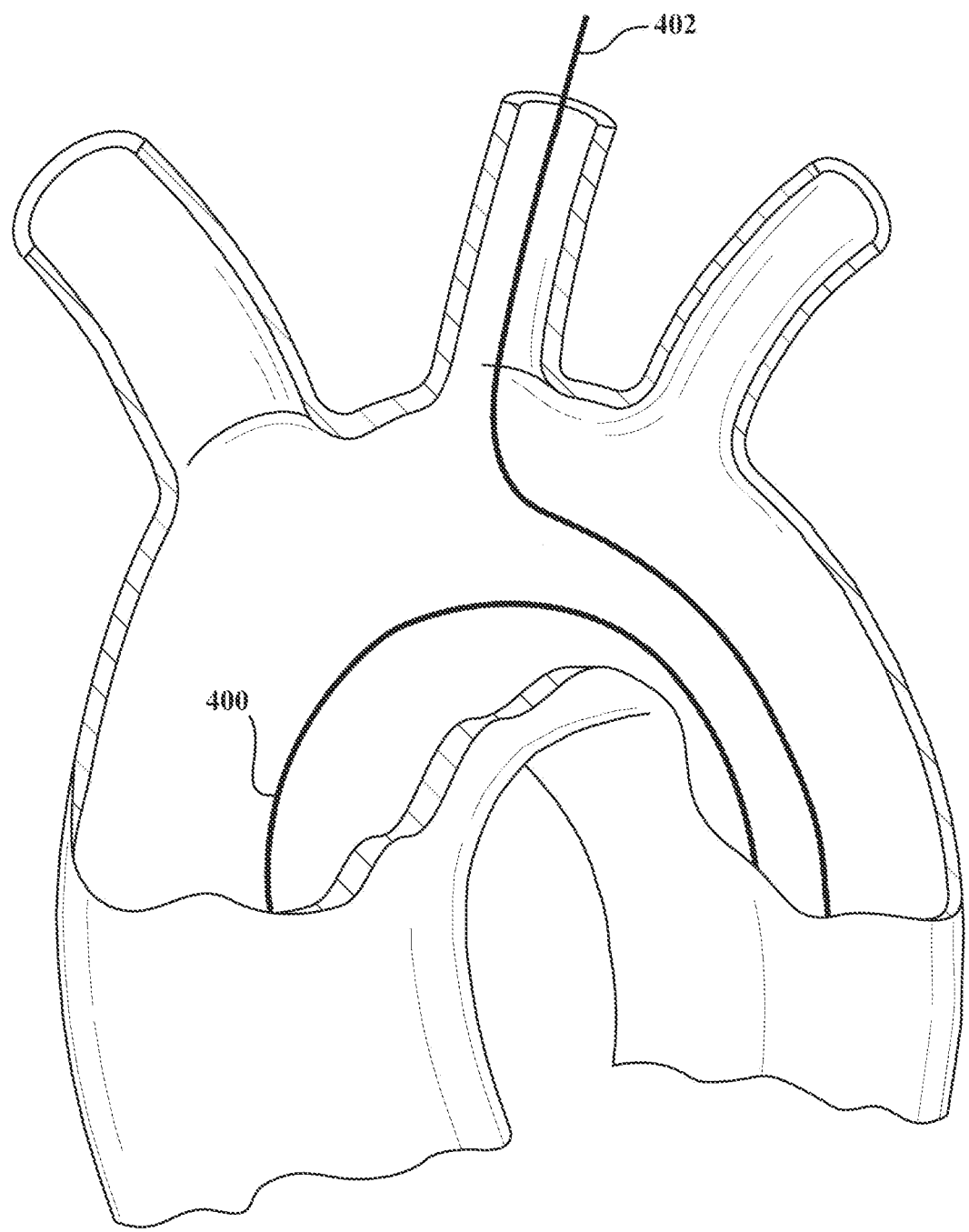
FIGS. 5-9 illustrate methods of deploying the main body and branch device in accordance with exemplary embodiments.

Referring to FIG. 5, a main guidewire 400 is routed to the aortic arch via the femoral artery. A first branch guidewire 402 is routed to the carotid artery via the femoral artery.

The main body of the device can be provided in a constrained state by a flexible primary sleeve on a proximal end of a catheter. A flexible secondary sleeve can be provided and disposed around the main body to constrain the main body in a partially deployed state after opening the primary sleeve to facilitate positioning of the device at the treatment prior to final deployment. Further detail of the sleeves, construction and deployment are provided in U.S. Pat. No. 5,919,225 to Lau et al., and U.S. Publication 2010/0049294 to Zukowski et al., the entire contents of which are incorporated herein by reference for all purposes.

Figure 6:
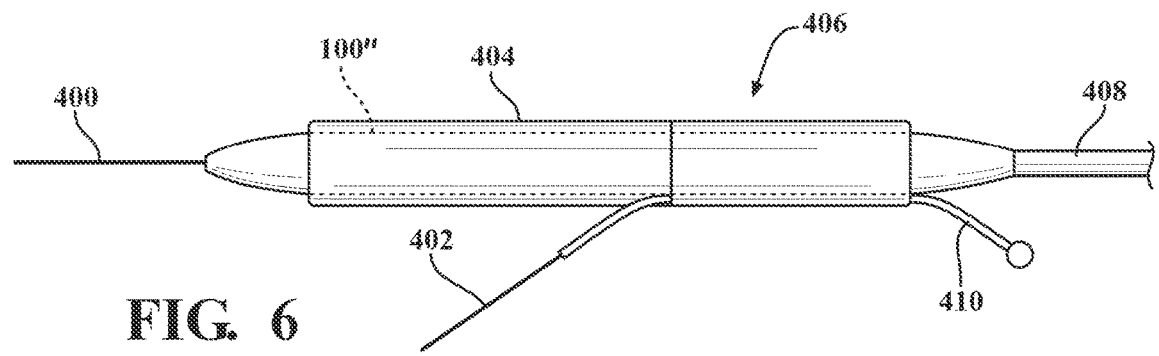

In a number of embodiments, for example as illustrated in FIG. 6, a guidewire tube or conduit 410 for each branch member to be deployed is positioned through the main lumen and each recess opening in the main body 100" and constrained together with the main body 100" by the primary sleeve 404. The guidewire tube or conduit 410 preserves a lumen through which a branch guidewire can be inserted while the main body 100" remains constrained by the primary sleeve 404. Further detail of the conduit, construction and deployment are provided in U.S. Patent Publication 2008/0269866 to Hamer et al., the entire content of which is incorporated herein by reference for all purposes.

Figure 7:
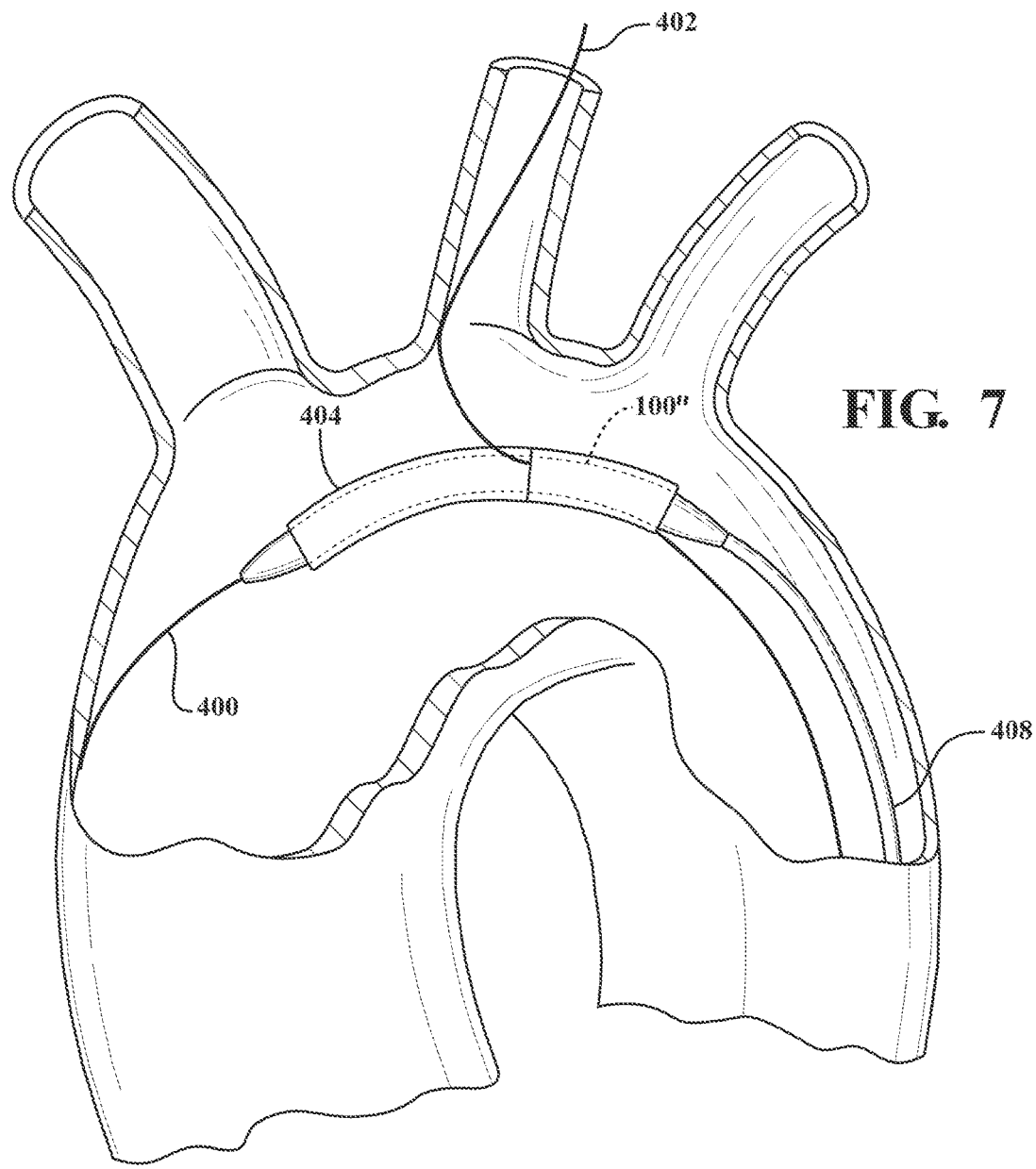

The main guidewire 400 is inserted through the main lumen. The first branch guidewire is inserted through the conduit 410 while the main body 100" and conduit 410 are constrained by the primary sleeve 100". As illustrated in FIG. 7, the constrained main body 100" is advanced along the respective main 400 and first branch 402 guidewires toward the treatment site. The conduit 410 is displaced from the main body 100" and remains outside of the body while the constrained main body 100" is advanced along the main 400 and first branch 402 guidewires toward the treatment site.

Figure 8:
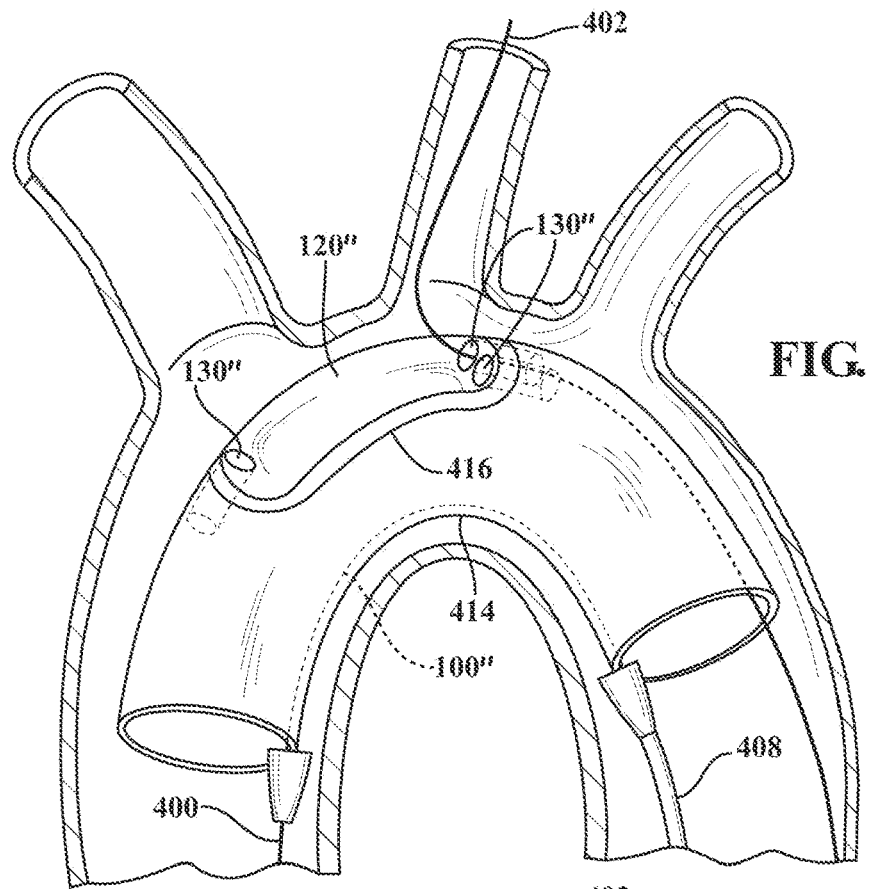

Referring to FIG. 8, the main body 100" is then partially deployed by opening the primary sleeve, thereby allowing the main body to expand outwardly until the main body is constrained by the secondary sleeve 414 to an intermediate peripheral dimension smaller than its fully deployed outer peripheral dimension. Maintaining the main body 100" in the intermediate peripheral dimension facilitates fine positioning of the device at the treatment site prior to full deployment.

With the recessed portion 120" of the main body now exposed, each opening in the recessed portion is then generally aligned with each branch vessel to be treated. The secondary sleeve 414 includes a window 416 aligned with the recessed portion 120" to allow access between the main lumen and the branch vessels to be treated. In other embodiments, a length of the main body along which the recessed portion is located can have a reduced diameter or outer peripheral dimension so as to facilitate access through the openings while the main body is in a partially deployed state in the secondary sleeve.

Figure 9:
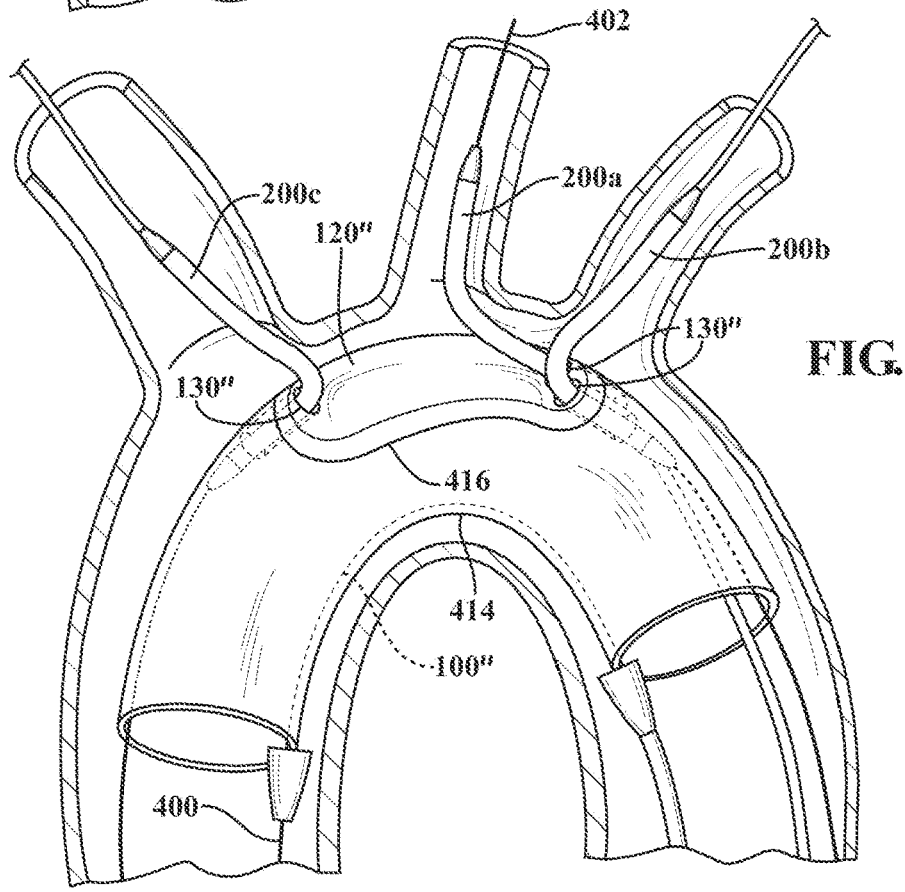

Referring to FIG. 9, a first branch member 200a of the device is provided in a constrained state on a proximal end of a first branch catheter utilizing a branch constraining sleeve, as described above for the main body. The first branch member is then advanced and positioned along the first branch guidewire through an opening 130" to one of the branch vessels along the aortic arch. The recessed portion facilitates routing and advancement of the first branch guidewire, as well as the constrained first branch member, to the branch vessel to be treated. As illustrated in FIG. 9, the first branch member is positioned for treatment of the left carotid artery.

Once the first branch member is in place, the main body is then fully deployed by opening the secondary sleeve. The first branch member can then be deployed by opening the branch constraining sleeve.

Still referring to FIG. 9, second 200b and third 200c branch members may also be delivered along respective second and third branch guidewires, as necessary, to other branch vessels. As shown, the second and third branch members can be positioned for treatment of the innominate and left subclavian arteries, respectively. Prior to advancement of the first branch member to the left carotid artery, as described above, a second branch guidewire can be routed via the innominate artery toward the aortic arch and into the main lumen via a second opening in the recessed portion. Similarly, a third branch guidewire can be routed via the left subclavian artery toward the aortic arch and into the main lumen via a third opening in the recessed portion.

The second 200b and third 200c branch members are then provided in constrained states each on a proximal end of respective second and third branch catheters utilizing branch constraining sleeves, as described above for the first branch member. The second and third branch members are then advanced and positioned along the second and third branch guidewires to the remaining branch arteries, which in the illustrated embodiment, are the innominate and left subclavian arteries, respectively.

Once all of the branch members 200a, 200b, 200c are in place, the main body is then fully deployed by opening the secondary sleeve. The first, second and third branch members can then be deployed by opening the respective branch constraining sleeves. The branch members may be deployed in any order as necessary, as dictated by the site and/or procedure.

Figure 10:
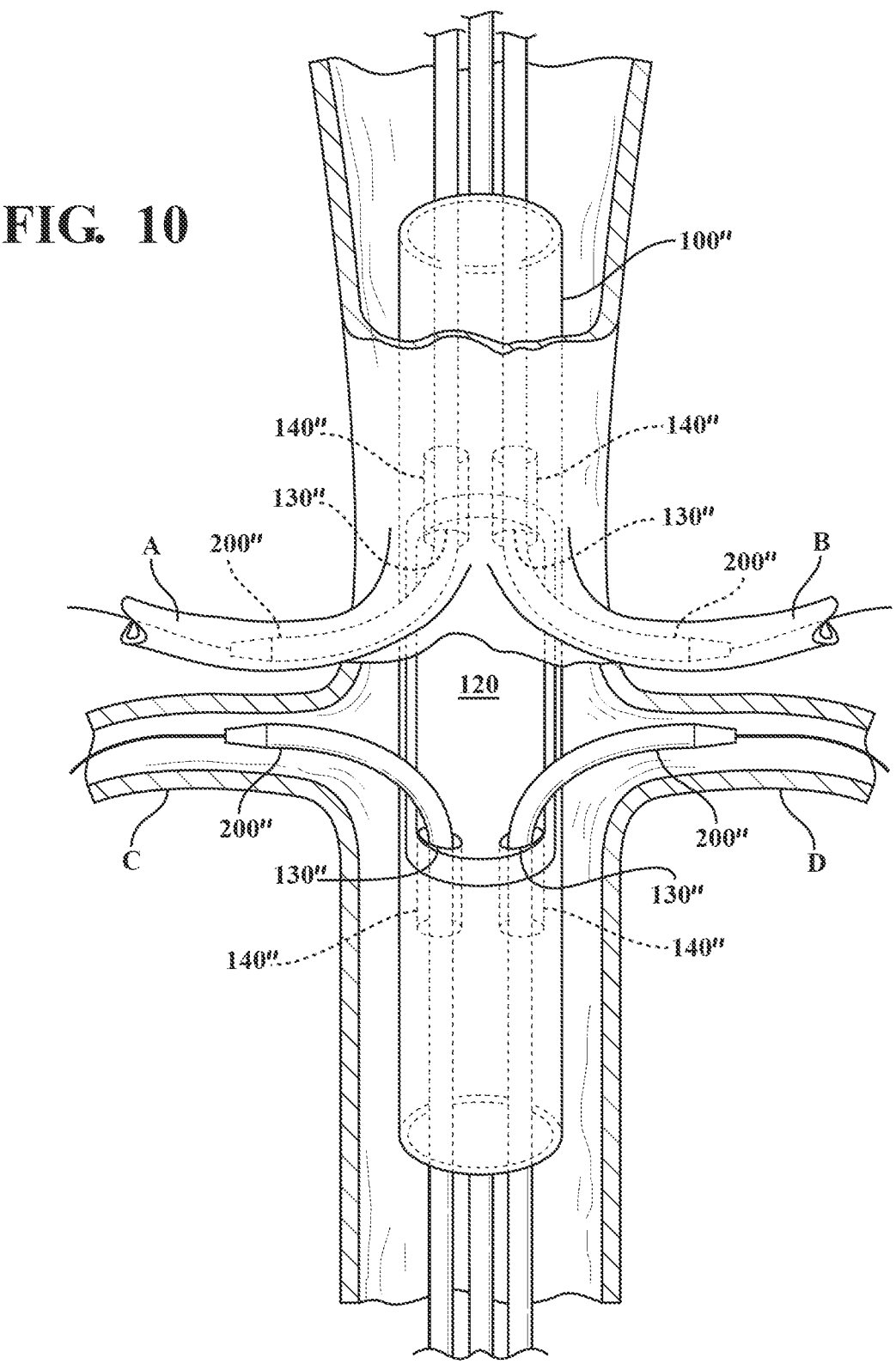
FIG. 10 is a perspective view of a main body of a branched device in accordance with exemplary embodiments for treating a vessel and branch vessels extending outwardly therefrom.

Referring to FIG. 10, in accordance with other exemplary embodiments, the main body 100" may include four openings 130" disposed in pairs arranged along opposite ends of the recessed portion 120" for deploying branch members 200" to treatment sites, for example, along the superior mesenteric, celiac, and renal arteries. The branch members 200" in this embodiment may be delivered and deployed to the respective branch vessels through the openings 130" in the recessed portion 120" of the main body 100" as described in above for the other exemplary embodiments. It should be appreciated that the number of openings and branch members can vary depending on the desired number of branch vessels to be treated.

In various embodiments, the wall or at least the recessed portion of the wall can be configured to allow the recessed portion to be displaced outwardly when pressure in the main lumen exceeds pressure outside of the main body, thereby allowing increased blood flow through the main lumen.

The devices, including the main bodies and branch members, described above may be made up of any material which is suitable for use as a graft or stent graft in the chosen body lumen. The grafts can be composed of the same or different materials. Furthermore, the grafts can comprise multiple layers of material that can be the same material or different material. Although the graft can have several layers of material, the graft may have a layer that is formed into a tube (innermost tube) and an outermost layer that is formed into a tube (outermost tube).

Many graft materials are known, particularly known are those that can be used as vascular graft materials. In one embodiment, the materials can be used in combination and assembled together to comprise a graft. The graft materials, used in a stent-graft, can be extruded, coated or formed from wrapped films, or a combination thereof. Polymers, biodegradable and natural materials can be used for specific applications.

Examples of synthetic polymers include, but are not limited to nylon, polyacrylamide, polycarbonate, polyformaldehyde, polymethylmethacrylate, polytetrafluoroethylene, polytrifluorochlorethylene, polyvinylchloride, polyurethane, elastomeric organosilicon polymers, polyethylene, polypropylene, polyurethane, polyglycolic acid, polyesters, polyamides, their mixtures, blends and copolymers are suitable as a graft material. In one embodiment, the graft is made from a class of polyesters such as polyethylene terephthalate including DACRON® and MYLAR® and polyaramids such as KEVLAR®, polyfluorocarbons such as polytetrafluoroethylene (PTFE) with and without copolymerized hexafluoropropylene (TEFLON® or GORE-TEX®), and porous or nonporous polyurethanes. In another embodiment, the graft comprises expanded fluorocarbon polymers (especially PTFE) materials. Included in the class of preferred fluoropolymers are polytetrafluoroethylene (PTFE), fluorinated ethylene propylene (FEP), copolymers of tetrafluoroethylene (TFE) and perfluoro (propyl vinyl ether) (PFA), homopolymers of polychlorotrifluoroethylene (PCTFE), and its copolymers with TFE, ethylenechlorotrifluoroethylene (ECTFE), copolymers of ethylene-tetrafluoroethylene (ETFE), polyvinylidene fluoride (PVDF), and polyvinylfluoride (PVF). Especially preferred, because of its widespread use in vascular prostheses, is ePTFE. In another embodiment, the graft comprises a combination of the materials listed above. In another embodiment, the graft is substantially impermeable to bodily fluids. The substantially impermeable graft can be made from materials that are substantially impermeable to bodily fluids or can be constructed from permeable materials treated or manufactured to be substantially impermeable to bodily fluids (e.g. by layering different types of materials described above or known in the art). In one embodiment, the main body and branch members, as described above, are made from any combinations of the materials above. In another embodiment, the main body and branch members, as described above, comprise ePTFE.

The stents, as described above, may be generally cylindrical when restrained and/or when unrestrained and comprise helically arranged undulations having plurality of helical turns. The undulations preferably are aligned so that they are "in-phase" with each other. More specifically, undulations comprise apices in opposing first and second directions. When the undulations are in-phase, apices in adjacent helical turns are aligned so that apices can be displaced into respective apices of a corresponding undulation in an adjacent helical turn. In one embodiment, the undulations have a sinusoidal shape. In another embodiment, the undulations are U shaped. In another embodiment, the undulations are V shaped. In another embodiment, the undulations are ovaloid shaped. These shapes are fully described in U.S. Pat. No. 6,042,605. U.S. Pat. No. 6,042,605 is incorporated by reference herein in its entirety for all purposes.

In another embodiment, the stents, as described above, may also be provided in the form of a series of rings arranged generally coaxially along the graft body.

In various embodiments, the stent can be fabricated from a variety of biocompatible materials including commonly known materials (or combinations of materials) used in the manufacture of implantable medical devices. Typical materials include 316L stainless steel, cobalt-chromium-nickel-molybdenum iron alloy ("cobalt-chromium"), other cobalt alloys such as L605, tantalum, nitinol, or other biocompatible metals. In one embodiment, any stent-graft described herein is a balloon expandable stent-graft. In another embodiment, any stent-graft described herein is a selfexpanding stent-graft. In another embodiment, the stent is a wire wound stent. In another embodiment, the wire wound stent comprise undulations.

Numerous characteristics and advantages of the present invention have been set forth in the preceding description, including preferred and alternate embodiments together with details of the structure and function of the invention. The disclosure is intended as illustrative only and as such is not intended to be exhaustive. It will be evident to those skilled in the art that various modifications may be made, especially in matters of structure, materials, elements, components, shape, size and arrangement of parts within the principals of the invention, to the full extent indicated by the broad, general meaning of the terms in which the appended claims are expressed. To the extent that these various modifications do not depart from the spirit and scope of the appended claims, they are intended to be encompassed therein. In addition to being directed to the embodiments described above and claimed below, the present invention is further directed to embodiments having different combinations of the features described above and claimed below. As such, the invention is also directed to other embodiments having any other possible combination of the dependent features claimed below. It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A device for treating disease along a main vessel and at least one branch vessel extending from the main vessel, the device comprising:
    a main body for deployment in the main vessel, the main body having an inflow end, an outflow end and a wall extending generally longitudinally between the inflow and outflow ends, the wall having an inner surface defining a main lumen and an outer surface opposite the inner surface, the main lumen allowing fluid flow therethrough, the wall having a recessed portion that is recessed relative to the outer surface of the wall and positioned between the inflow and outflow ends of the main body;
    a first pair of support members including a first support member and a second support member, the first pair of support members arranged within the recessed portion of the wall and extending toward one of the outflow and inflow ends of the main body, the first pair of support members each forming a secondary lumen; and
    a second pair of support members including a third support member and fourth support member, the second pair of support members arranged within the recessed portion of the wall and extending toward one of the outflow end and inflow end of the main body, the second pair of support members each forming a secondary lumen,
    wherein the first pair of support members and the second pair of support members are longitudinally offset from each other along a length of the main body.

2. The device of claim 1, wherein the first pair of support members and the second pair of support members are positioned on opposing ends of the recessed portion of the wall.

3. The device of claim 1, wherein the first pair of support members and the second pair of support members extend parallel to the main body.

4. The device of claim 1, wherein the first pair of secondary lumens and the second pair of secondary lumens extend parallel to the main lumen of the main body.

5. The device of claim 1,, wherein the first pair of support members are generally across from the second pair of support members such that the first and third support members are aligned with each other and the second and fourth support members are aligned with each other.

6. The device of claim 1, wherein the first pair of support members and the second pair of support members are generally tubular support members.

7. The device of claim 1, wherein the first support member is configured to receive a first branch member within the secondary lumen and the second support member is configured to receive a second branch member within the secondary lumen.

8. The device of claim 7, wherein the first branch member and the second branch member extend outwardly from the main body through the recessed portion of the wall and the first branch member extends into a first branch vessel and the second branch member extends into a second branch vessel.

9. The device of claim 8, wherein the main vessel is a superior mesenteric artery and the first branch vessel and the second branch vessel are both celiac arteries.

10. The device of claim 1, wherein the third support member is configured to receive a third branch member within the secondary lumen and the fourth support member is configured to receive a fourth branch member within the secondary lumen.

11. The device of claim 10, wherein the third branch member and the fourth branch member extend outwardly from the main body through the recessed portion and the third branch member extends into a third branch vessel and the fourth branch member extends into a fourth branch vessel.

12. The device of claim 11, wherein the main vessel is a superior mesenteric artery and the third branch vessel and the fourth branch vessel are both renal arteries.

13. A device for treating disease along a main vessel and at least one branch vessel extending from the main vessel, the device comprising:
    a main body for deployment in the main vessel, the main body having an inflow end and an outflow end and a wall extending generally longitudinally between the inflow and outflow ends, the wall having an inner surface defining a main lumen and an outer surface opposite the internal surface, the main lumen allowing fluid flow therethrough, the wall having a recessed portion that is recessed relative to the outer surface of the wall and positioned between the inflow and outflow ends of the main body;
    a first pair of openings including a first opening and a second opening, the first pair of openings being arranged within the recessed portion of the wall and extending toward one of the outflow and inflow ends of the main body, the first pair of openings being generally cylindrical; and
    a second pair of openings including a third opening and a fourth opening, the second pair of openings being arranged within the recessed portion of the wall and extending toward one of the outflow and inflow ends of the main body, the second pair of openings being generally cylindrical,
    wherein the first pair of openings and the second pair of openings are longitudinally offset from each other along a length of the main body.

14. The device of claim 13, wherein the first pair of openings and the second pair of openings are generally arranged across from one another such that the first opening and the third opening are aligned with each other and the second opening and the fourth opening are aligned with each other.

15. The device of claim 13, wherein the first pair of openings and the second pair of openings are arranged on opposing ends of the recessed portion of the wall.

16. The device of claim 13, wherein the first opening is configured to receive a first branch member and the second opening is configured to receive a second branch member.

17. The device of claim 16, wherein the main vessel is a superior mesenteric artery and the first branch member is configured to be received within a first celiac artery and the second branch member is configured to be received within a second celiac artery.

18. The device of claim 13, wherein the third opening is configured to receive a third branch member and the fourth opening is configured to receive a fourth branch member.

19. The device of claim 18, wherein the main vessel is a superior mesenteric artery and the third branch member is configured to be received within a first renal artery and the second branch member is configured to be received within a second renal artery.

20. A method for deploying a device to a treatment site for treating disease along a main vessel and at least one branch vessel extending from the main vessel, the method comprising:
    positioning the device in a constrained state into the main vessel such that the device is positioned proximate to the at least one branch vessel, the device including,
      a main body having an inflow end, an outflow end and a wall extending generally longitudinally between the inflow and outflow ends, the wall having an inner surface defining a main lumen and an outer surface opposite the inner surface, the main lumen allowing fluid flow therethrough, the wall having a recessed portion that is recessed relative to the outer surface of the wall and positioned between the inflow and outflow ends of the main body, and
      a first pair of support members including a first support member and a second support member, the first pair of support members arranged within the recessed portion of the wall and extending toward one of the outflow and inflow ends of the main body, and
      a second pair of support members including a third support member and fourth support member, the second pair of support members arranged within the recessed portion of the wall and extending toward one of the outflow and inflow ends of the main body,
      wherein the first pair of support members and the second pair of support members are longitudinally offset from each other along a length of the main body;
    partially deploying the device to a partially deployed state by releasing a primary sleeve;
    advancing a first pair of branch members through the first pair of support members while the device is in the partially deployed state; and
    fully deploying the device by releasing a secondary sleeve.

21. The method of claim 20, wherein the main vessel is superior mesenteric artery and the method further includes positioning the first pair of branch members within a pair of celiac arteries.

22. The method of claim 20, wherein the method further includes advancing a second pair of branch members through the second pair of support members while the device is in the partially deployed state.

23. The method of claim 22, wherein the main vessel is superior mesenteric artery and the method further includes positioning the second pair of branch members within a pair of renal arteries.

* * * * *